United States Patent
Man

(10) Patent No.: US 8,853,629 B2
(45) Date of Patent: Oct. 7, 2014

(54) CROSS-SECTION PROCESSING AND OBSERVATION METHOD AND CROSS-SECTION PROCESSING AND OBSERVATION APPARATUS

(71) Applicant: Hitachi High-Tech Science Corporation, Tokyo (JP)

(72) Inventor: Xin Man, Tokyo (JP)

(73) Assignee: Hitachi High-Tech Science Corporation (JP)

( * ) Notice: Subject to any disclaimer, the term of this patent is extended or adjusted under 35 U.S.C. 154(b) by 0 days.

(21) Appl. No.: 13/845,608

(22) Filed: Mar. 18, 2013

(65) Prior Publication Data

US 2013/0248708 A1   Sep. 26, 2013

(30) Foreign Application Priority Data

Mar. 22, 2012   (JP) .................................. 2012-065974

(51) Int. Cl.
- H01J 37/22 (2006.01)
- H01J 37/305 (2006.01)
- G01N 23/22 (2006.01)
- G01N 1/32 (2006.01)

(52) U.S. Cl.
CPC ........ H01J 37/3053 (2013.01); G01N 23/2202 (2013.01); G01N 1/32 (2013.01); H01J 2237/226 (2013.01); H01J 2237/31745 (2013.01)
USPC ...................................... 250/307; 250/492.3

(58) Field of Classification Search
CPC ... H01J 32/222; H01J 37/222; H01J 37/3053; H01J 37/31; G01N 23/2202; G01N 1/22
USPC .............................................. 250/307, 492.3
See application file for complete search history.

(56) References Cited

U.S. PATENT DOCUMENTS

| | | | | |
|---|---|---|---|---|
| 6,300,631 | B1 * | 10/2001 | Shofner | 250/311 |
| 6,888,136 | B2 * | 5/2005 | Geurts et al. | 250/307 |
| 2008/0035860 | A1 * | 2/2008 | Hill et al. | 250/492.3 |
| 2009/0242759 | A1 * | 10/2009 | Bray et al. | 250/307 |
| 2010/0080446 | A1 * | 4/2010 | Herschbein et al. | 382/149 |
| 2011/0204225 | A1 * | 8/2011 | Shichi et al. | 250/310 |
| 2012/0273692 | A1 * | 11/2012 | Tokuda et al. | 250/400 |
| 2012/0326028 | A1 * | 12/2012 | Muto et al. | 250/307 |
| 2013/0228953 | A1 * | 9/2013 | Ikeda et al. | 264/401 |

FOREIGN PATENT DOCUMENTS

JP   2008 270073   11/2008

* cited by examiner

*Primary Examiner* — Nicole Ippolito
*Assistant Examiner* — Wyatt Stoffa
(74) *Attorney, Agent, or Firm* — Adams & Wilks

(57) ABSTRACT

A cross-section processing and observation method including: acquiring a surface image by scanning and irradiating a surface of a sample with ion beam; setting, on the surface image, a first sliced region and a second sliced region for performing the slice processing, the second sliced region being adjacent to the first sliced region and having a longitudinal length obtained by subtracting a slice width of the second sliced region from a longitudinal length of the first sliced region; forming a cross-section by irradiating the first sliced region and the second sliced region with the ion beam; and acquiring a cross-sectional image by irradiating the cross-section with electron beam.

5 Claims, 5 Drawing Sheets

CROSS-SECTION PROCESSING AND OBSERVATION METHOD AND CROSS-SECTION PROCESSING AND OBSERVATION APPARATUS

CROSS-REFERENCE TO RELATED APPLICATIONS

This application claims priority from Japanese Patent Application No. 2012-065974 filed on Mar. 22, 2012, the entire contents of which are incorporated herein by reference.

TECHNICAL FIELD

Aspects of the present invention relate to a cross-section processing and observation method of forming a cross-section by a focused ion beam and observing the cross-section by an electron beam.

BACKGROUND

As a method of analyzing internal structure and defects in a semiconductor device or the like, there is known a cross-section processing and observation method in which a focused ion beam is used for cross-section processing and slicing of a sample to expose a cross-section including a desired structure or a defect, and a scanning electron microscope is used to observe the cross-section. According to this method, an observation target inside the sample can be exposed with pinpoint accuracy, and hence the structure or the defect can be observed quickly.

There is disclosed a method of repeatedly performing cross-section processing and cross-section observation and combining a plurality of acquired cross-sectional observation images to construct a three-dimensional image of a region subjected to the cross-section processing (see JP-A-2008-270073). According to this method, a three-dimensional image of an observation target can be constructed.

Recently, along with densification and reduction in size of semiconductor devices, a device pattern has become finer, and hence, cross-section processing and observation for a minute observation target have been required. In this case, by setting a gap between one cross-section and another cross-section formed by subjecting the one cross-section to slice processing to be extremely small, that is, by reducing a slice width of a focused ion beam, a minute observation target can be exposed in the cross-section and observed.

However, if the slice width is extremely small, it is difficult to measure the width, and hence there has been a problem in reliability of acquired data. For example, it cannot be confirmed whether or not an observation image acquired by a cross-section processing and observation with a slice width of 1 nm is an observation image photographed with an actual slice width of 1 nm. Thus, there has been a problem in that it is difficult to measure an actual shape from the observation image.

SUMMARY

Aspects of the present invention provide a cross-section processing and observation method and a cross-section processing and observation apparatus, by which a slice width can be measured even when the slice width is minute and highly-reliable observation data can be acquired.

According to an aspect of the present invention, there is provided a cross-section processing and observation method in which slice processing on a sample by irradiation of an ion beam to the sample to form a cross-section and acquisition of a cross-sectional image by irradiation of an electron beam to the cross-section are repeatedly performed, the method including: acquiring a surface image by scanning and irradiating a surface of the sample with the ion beam; setting, on the surface image, a first sliced region and a second sliced region for performing the slice processing, the second sliced region being adjacent to the first sliced region and having a longitudinal length obtained by subtracting a slice width of the second sliced region from a longitudinal length of the first sliced region; forming the cross-section by irradiating the first sliced region and the second sliced region with the ion beam; and acquiring the cross-sectional image by irradiating the cross-section with the electron beam.

According to another aspect of the present invention, there is provided a cross-section processing and observation apparatus including: an ion beam column configured to irradiate a surface of a sample with an ion beam to form a cross-section to the sample; an electron beam column configured to irradiate the cross-section with an electron beam to acquire an observation image of the cross-section; a detector configured to detect a charged particle generated from the sample; an image forming portion configured to form an observation image of the sample based on a detection signal of the detector; and a sliced region setting portion configured to set, on the observation image of the surface of the sample, a first sliced region and a second sliced region for performing slice processing on the sample, the second sliced region being adjacent to the first sliced region and having a longitudinal length obtained by subtracting a slice width of the second sliced region from a longitudinal length of the first sliced region.

Accordingly, the slice width actually subjected to slice processing can be measured from the cross-sectional image. Therefore, the slice width can be measured with high accuracy.

According to the cross-section processing and observation method and the cross-section processing and observation apparatus of the present invention, even when the slice width is minute, the slice width can be measured to acquire highly-reliable observation data.

DETAILED DESCRIPTION

Figure 1:
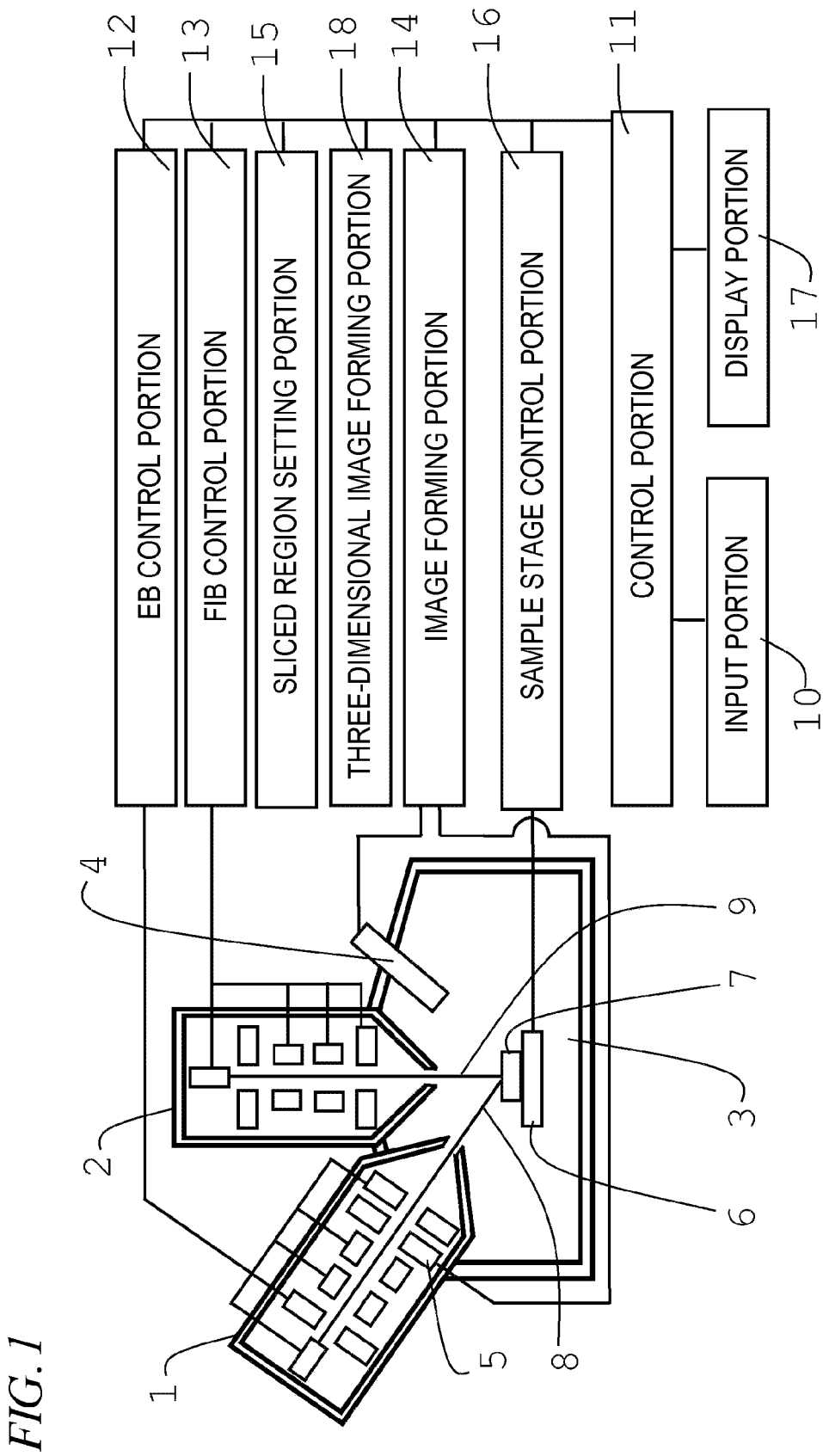
FIG. 1 is a configuration diagram of a cross-section processing and observation apparatus according to an exemplary embodiment of the present invention.

A cross-section processing and observation method and a cross-section processing and observation apparatus according to an exemplary embodiment of the present invention will be described hereinafter., As illustrated in FIG. 1, the cross-section processing and observation apparatus in this exemplary embodiment includes an EB column 1, a FIB column 2, and a sample chamber 3. The EB column 1 and the FIB column 2 irradiate a sample 7 accommodated in the sample chamber 3 with an electron beam 8 and an ion beam 9, respectively.

The sample processing apparatus further includes a secondary electron detector 4 and a backscattered electron detector 5 as charged particle detectors. The secondary electron detector 4 is capable of detecting secondary electrons generated from the sample 7 by irradiation of the electron beam 8 or the ion beam 9. The backscattered electron detector 5 is provided inside the EB column 1. The backscattered electron detector 5 is capable of detecting backscattered electrons reflected by the sample 7 as a result of the irradiation of the electron beam 8 to the sample 7.

The cross-section processing and observation apparatus further includes a sample stage 6 for placing the sample 7 thereon. The sample stage 6 can be tilted to change an incident angle of the ion beam 9 to the sample 7. The tilt of the sample stage 6 is controlled by a sample stage control portion 16.

The cross-section processing and observation apparatus further includes an EB control portion 12, a FIB control portion 13, an image forming portion 14, and a display portion 17. The EB control portion 12 transmits an irradiation signal to the EB column 1 to control the EB column 1 to radiate the electron beam 8. The FIB control portion 13 transmits an irradiation signal to the FIB column 2 to control the FIB column 2 to radiate the ion beam 9. The image forming portion 14 forms a backscattered electron image based on a signal for scanning the electron beam 8 sent from the EB control portion 12 and a signal of the backscattered electrons detected by the backscattered electron detector 5. The display portion 17 is capable of displaying the backscattered electron image. The image forming portion 14 forms data of a SEM image based on the signal for scanning the electron beam 8 sent from the EB control portion 12 and a signal of the secondary electrons detected by the secondary electron detector 4. The display portion 17 is capable of displaying the SEM image. Further, the image forming portion 14 forms data of a SIM image based on a signal for scanning the ion beam 9 sent from the FIB control portion 13 and a signal of the secondary electrons detected by the secondary electron detector 4. The display portion 17 is capable of displaying the SIM image.

The cross-section processing and observation apparatus further includes an input portion 10 and a control portion 11. An operator inputs conditions on the apparatus control, such as a beam irradiation condition, to the input portion 10. The input portion 10 transmits the input information to the control portion 11. The control portion 11 transmits a control signal to the EB control portion 12, the FIB control portion 13, the image forming portion 14, the sample stage control portion 16, or the display portion 17, to thereby control the operation of the cross-section processing and observation apparatus.

Description is given to the control of the apparatus. For example, the operator sets an irradiation region of the ion beam 9 based on an observation image displayed on the display portion 17, such as the backscattered electron image, the SEM image, or the SIM image. The operator inputs, via the input portion 10, a processing frame for setting the irradiation region on the observation image displayed on the display portion 17. The processing frame as used herein is a frame indicating a boundary between a region to be irradiated with the ion beam 9 and a region not to be irradiated with the ion beam 9. When the operator inputs an instruction to start processing to the input portion 10, a signal indicating the irradiation region and a signal indicating the start of processing are transmitted from the control portion 11 to the FIB control portion 13, and the FIB control portion 13 radiates the ion beam 9 to the specified irradiation region of the sample 7. In this manner, the irradiation region input by the operator can be irradiated with the ion beam 9.

The cross-section processing and observation apparatus further includes a sliced region setting portion 15 for setting, on the SIM image, a sliced region for performing slice processing.

Additionally, the cross-section processing and observation apparatus further includes a three-dimensional image forming portion 18 for constructing a three-dimensional image of the sample based on acquired SEM images and the slice width.

Figure 2A:
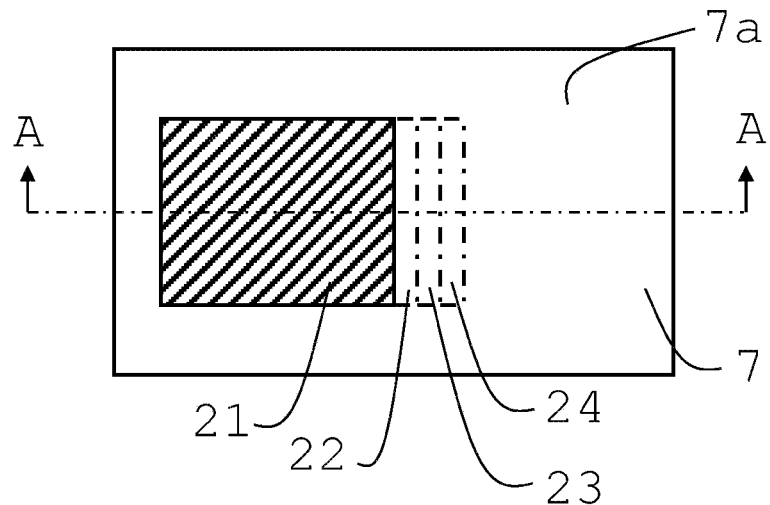
FIGS. 2A and 2B are explanatory diagrams of a cross-section processing and observation method according to the exemplary embodiment of the present invention.
Figure 2B:
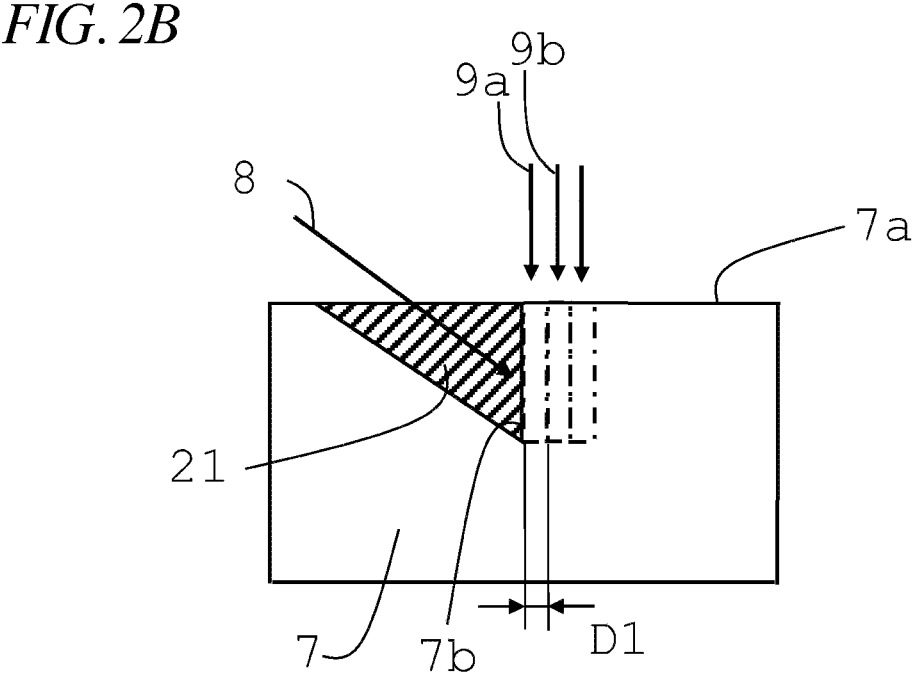

Next, a cross-section processing and observation method in this exemplary embodiment is described. As illustrated in FIG. 2A, a processing groove 21 is formed in the sample 7 so that a cross-section may be irradiated with the electron beam 8 for observing the cross-section. A surface 7a of the sample 7 is scanned and irradiated with the ion beam 9 to form the processing groove 21 by etching processing. FIG. 2B is a cross-sectional diagram taken along the line A-A of FIG. 2A. The processing groove 21 is formed into a slope shape so that a cross-section 7b may be scanned and irradiated with the electron beam 8. The slope shape can reduce the amount of etching and shorten a processing time as compared with the case of forming a box-shape groove.

Then, slice processing and observation of a cross-section exposed by the slice processing are repeatedly performed. In other words, a sliced region 22 is scanned and irradiated with an ion beam 9a to perform etching processing, and a cross-section exposed by the processing is scanned and irradiated with the electron beam 8 to acquire a SEM image. Next, a sliced region 23 is scanned and irradiated with an ion beam 9b to perform etching processing so that the next cross-section is exposed to acquire a SEM image. In this manner, SEM images of a plurality of cross-sections can be acquired at an interval of a width D1 of the sliced region. Based on the SEM images, the internal structure of the sample 7 can be analyzed.

The sliced region is subjected to etching processing by the ion beam 9, and hence, a portion of the sample within the width D1 of the sliced region does not appear in the SEM image. Therefore, in order to observe a minute observation target, it is necessary to set the width D1 of the sliced region to be smaller than the target. However, the set width of the sliced region and an actually etched slice width are not always the same. This is because the etching rate differs depending on the material and structure of a sample to be etched.

Therefore, it is necessary to measure the actually etched slice width. The sliced region is scanned and irradiated with the ion beam 9 in a direction perpendicular to the surface 7a of the sample 7, and a SIM image is observed to measure the slice width. However, in the case where the slice width is minute, in particular in the case where the slice width is equal to or smaller than a beam diameter of the ion beam 9, for example, 5 nm or less, it is difficult to measure the slice width from the SIM image.

Figure 3A:
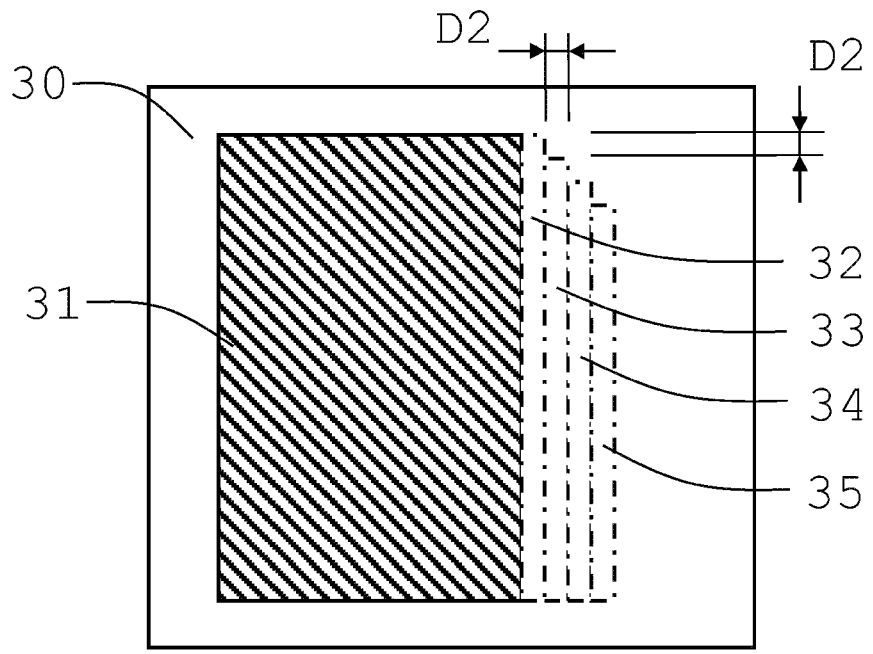
FIGS. 3A and 3B are explanatory diagrams of the cross-section processing and observation method according to the exemplary embodiment of the present invention.
Figure 3B:
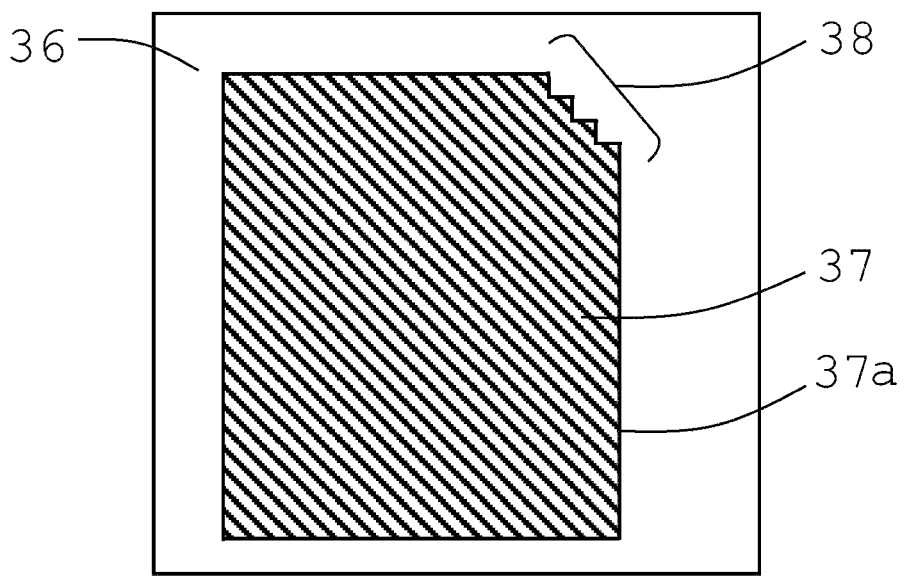

In view of the above, the sample processing method in this exemplary embodiment uses a slice width measuring method described hereinafter. In the slice width measuring method, as illustrated in FIGS. 3A and 3B, the sliced region is set and processed so that the length of the sliced region is shorter by the width of the sliced region. Then, a cross-section formed by the processing is observed by SEM. In the SEM observation, minute unevenness in the cross-section can be observed, and hence, a minute step formed in the cross-section and having the same length as the slice width can be observed. In this manner, the slice width can be measured from the SEM image of the cross-section.

FIG. 3A is a SIM image 30 of the surface 7a of the sample 7. A processing groove 31 is formed. In the SIM image 30, sliced regions 32, 33, 34, and 35 are set by the sliced region setting portion 15. The longitudinal length of each of the sliced regions 33, 34, and 35 is set so as to be a length obtained by subtracting the width of the sliced region from the longitudinal length of a sliced region adjacent thereto on the processing groove 31 side. For example, the sliced region 33 has a length obtained by subtracting a width D2 of the sliced region 33 from the length of the sliced region 32. Then, the set sliced regions 32, 33, 34, and 35 are scanned and irradiated with the ion beam 9, to thereby perform cross-section processing and observation.

FIG. 3B is a SIM image 36 after etching processing. A processing groove 37 has a step shape 38 because the sliced regions having different lengths are used.

Figure 4:
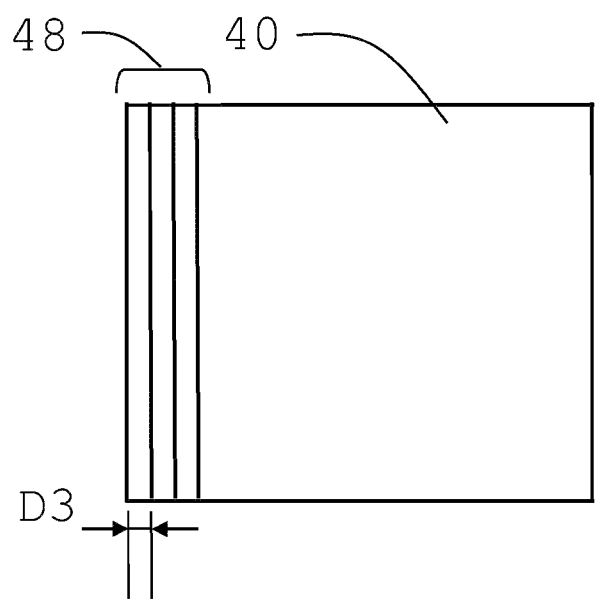
FIG. 4 is an explanatory diagram of the cross-section processing and observation method according to the exemplary embodiment of the present invention.

FIG. 4 is a SEM image 40 of a cross-section 37a acquired by scanning and irradiation of the electron beam 8. In the SEM image 40, a shape 48 resulting from the step shape 38 appears. Based on the width of the shape 48, the slice width can be measured. For example, the value of a width D3 measured from the SEM image 40 can be regarded as an actually etched slice width. In this manner, the slice width by which the sample 7 is actually subjected to etching processing by the ion beam 9 can be measured.

Next, description is given to a method of constructing a three-dimensional image of a region subjected to cross-section processing, based on SEM images of a plurality of cross-sections acquired by cross-section processing and observation and the actually etched slice width obtained by the slice width measuring method.

Figure 5:
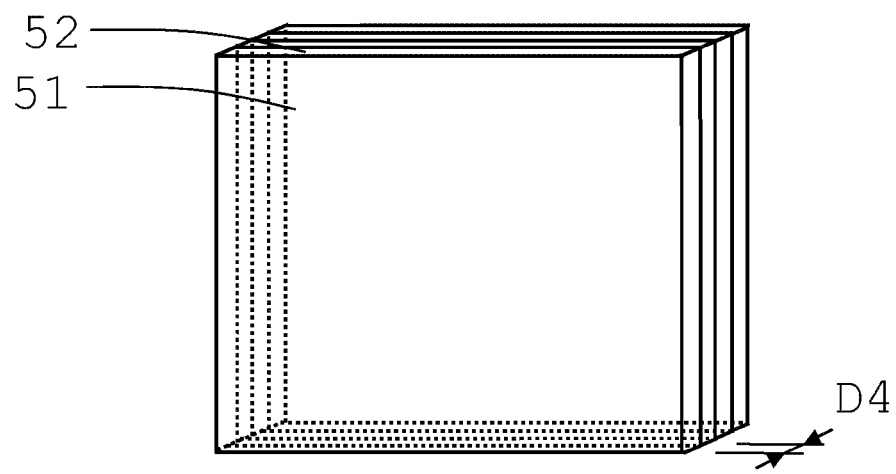
FIG. 5 is an explanatory diagram of the cross-section processing and observation method according to the exemplary embodiment of the present invention.

As illustrated in FIG. 5, a plurality of acquired SEM images are arranged at an interval based on the actually etched slice width. Specifically, a SEM image 51 and a SEM image 52 are arranged at an interval of the length obtained by multiplying a slice width D4 obtained by the above-mentioned slice width measuring method by a display magnification of the SEM images. Other SEM images are arranged in the same way. In this manner, a three-dimensional image of the region subjected to cross-section processing can be constructed.

What is claimed is:

1. A cross-section processing and observation method in which slice processing on a sample by irradiation of an ion beam to the sample to form a cross-section and acquisition of a cross-sectional image by irradiation of an electron beam to the cross-section are repeatedly performed, the method comprising:
   acquiring a surface image by scanning and irradiating a surface of the sample with the ion beam;
   setting, on the surface image, a first sliced region and a second sliced region for performing the slice processing, the second sliced region being adjacent to the first sliced region and having a longitudinal length obtained by subtracting a slice width of the second sliced region from a longitudinal length of the first sliced region;
   forming the cross-section by irradiating the first sliced region and the second sliced region with the ion beam; and
   acquiring the cross-sectional image by irradiating the cross-section with the electron beam.

2. The cross-section processing and observation method according to claim 1, further comprising:
   acquiring the cross-sectional image including a step structure formed by subjecting the first sliced region and the second sliced region to etching processing, and measuring the slice width of the second sliced region being subjected to the etching processing.

3. The cross-section processing and observation method according to claim 2, further comprising:
   constructing a three-dimensional image of the sample based on the cross-sectional images and the slice width.

4. A cross-section processing and observation apparatus comprising:
   an ion beam column configured to irradiate a surface of a sample with an ion beam to form a cross-section to the sample;
   an electron beam column configured to irradiate the cross-section with an electron beam to acquire an observation image of the cross-section;
   a detector configured to detect a charged particle generated from the sample;
   an image forming portion configured to form an observation image of the sample based on a detection signal of the detector; and
   a sliced region setting portion configured to set, on the observation image of the surface of the sample, a first sliced region and a second sliced region for performing slice processing on the sample, the second sliced region being adjacent to the first sliced region and having a longitudinal length obtained by subtracting a slice width of the second sliced region from a longitudinal length of the first sliced region.

5. The cross-section processing and observation apparatus according to claim 4, further comprising:
   a three-dimensional image forming portion configured to form a three-dimensional image of a region subjected to the slice processing based on a length of the slice width and a plurality of the observation images of the cross-sections formed by the slice processing.

* * * * *